(12) United States Patent
Loesel et al.

(10) Patent No.: US 7,390,089 B2
(45) Date of Patent: Jun. 24, 2008

(54) DEVICE AND METHOD FOR ALIGNING AN EYE WITH A SURGICAL LASER

(75) Inventors: Frieder Loesel, Mannheim (DE); Fritz Meisel, Kalchreuth (DE); Bernhard Gress, Dossenheim (DE); Tobias Kuhn, Jena (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 289 days.

(21) Appl. No.: 11/066,726

(22) Filed: Feb. 25, 2005

(65) Prior Publication Data
US 2006/0192921 A1 Aug. 31, 2006

(51) Int. Cl.
*A61B 3/00* (2006.01)
(52) U.S. Cl. .............................. 351/208; 606/4; 606/11
(58) Field of Classification Search ................. 351/219, 351/200, 205, 208, 209, 246; 606/4–6, 10–12, 606/166
See application file for complete search history.

(56) References Cited

U.S. PATENT DOCUMENTS

| 4,443,075 | A | 4/1984 | Crane |
| 4,702,575 | A | 10/1987 | Breglia |
| 4,718,418 | A | 1/1988 | L'Esperance, Jr. |
| 4,848,340 | A | 7/1989 | Bille et al. |
| 4,891,043 | A | 1/1990 | Zeimer et al. |
| 4,905,711 | A | 3/1990 | Bennett et al. |
| 5,108,412 | A | 4/1992 | Krumeich et al. |
| 5,336,215 | A | 8/1994 | Hsueh et al. |
| 5,450,144 | A | * 9/1995 | Ben Nun ..................... 351/219 |
| 5,549,632 | A | 8/1996 | Lai |
| 6,099,522 | A | * 8/2000 | Knopp et al. ................. 606/10 |
| 6,210,401 | B1 | * 4/2001 | Lai .............................. 606/12 |
| 6,280,436 | B1 | 8/2001 | Freeman et al. |
| 6,299,307 | B1 | 10/2001 | Oltean et al. |
| 6,373,571 | B1 | * 4/2002 | Juhasz et al. ................ 356/399 |
| 6,730,074 | B2 | 5/2004 | Bille et al. |
| 2004/0044333 | A1 | * 3/2004 | Sugiura ......................... 606/4 |
| 2004/0070761 | A1 | 4/2004 | Horvath et al. |

FOREIGN PATENT DOCUMENTS

| EP | 1159986 A2 | 12/2001 |
| EP | 1570822 A1 | 9/2005 |
| JP | 2004089215 A | * 3/2004 |
| WO | 0059402 | 10/2000 |

\* cited by examiner

*Primary Examiner*—Ricky L Mack
*Assistant Examiner*—James R Greece
(74) *Attorney, Agent, or Firm*—Nydegger & Associates

(57) ABSTRACT

A device for establishing a desired alignment between a patient's eye and a laser system to facilitate an engagement therebetween includes a light source to illuminate the eye. A moveable platform is provided to move the patient relative to the laser system. To establish alignment between the eye and the laser system, a reference marker is based on the laser system. An image of the marker, along with reflections from the illuminated eye, is then transmitted to the system controller. There, the image and reflections are processed to determine a measured alignment that is then compared to the desired alignment. An error signal that is indicative of an alignment difference is then generated and used to incrementally move the platform, or the patient, in an appropriate direction.

18 Claims, 2 Drawing Sheets

DEVICE AND METHOD FOR ALIGNING AN EYE WITH A SURGICAL LASER

FIELD OF THE INVENTION

The present invention pertains generally to devices and methods for performing ocular laser surgery. More particularly, the present invention pertains to devices for positioning the eye of a patient for laser surgery. The present invention is particularly, but not exclusively, useful as a device for establishing a contact alignment between a patient's eye and a laser system to facilitate the engagement of the eye with the laser system prior to a refractive laser surgery procedure.

BACKGROUND OF THE INVENTION

Surgical lasers are now commonly used in a variety of ophthalmic applications, including the diagnosis and treatment of ocular diseases, as well as the diagnosis and correction of optical deficiencies. As an example, corneal reshaping procedures using lasers, such as the well known LASIK procedure, are now widely available. In all of these procedures, the surgical laser is chosen as the tool of choice because of the ability of the laser to be accurately focused on extremely small amounts of ocular tissue. In addition, the ability of the laser to be guided to prescribed locations within the eye with precision and reliability has enabled a whole new class of ophthalmic procedures that require nothing short of pinpoint accuracy. Unfortunately, movements of the eye relative to the laser source can undermine the accuracy of the laser and reduce the efficacy of the laser procedure.

With the above in mind, movements of the eye can be classified broadly into two groups, namely, voluntary movements and involuntary movements. Voluntary movements can often be almost completely eliminated in most patients by instructing the patient to concentrate (i.e. fixate) on a target such as a small light source. On the other hand, involuntary eye movements cannot be remedied by instruction, and as a consequence, they must be somehow controlled. Included in the involuntary eye movements are movements due to the patient's pulse, movements due to the patient breathing, and psychotic eye movements which can occur, for example, when a patient is startled.

It can be easily appreciated that these involuntary movements can have an adverse effect on a laser operation unless the movements are either compensated for, or effectively eliminated. With regard to the former, eye tracking systems have been proposed to compensate for eye movement during a procedure. In simple terms, these tracking systems measure movements of the eye during a procedure and provide a real time signal indicating eye position to the laser system. In response to the signal, the laser system moves, and in some cases reshapes, the laser beam to follow the movements of the eye. Unfortunately, these eye tracking systems tend to be overly complicated, and, as a practical matter, do not always provide the reliability that is required for certain types of procedures. For example, for procedures wherein the laser is configured to ablate and destroy selected tissue, an error or malfunction of the tracking system can result in the immediate destruction of non-target tissue.

Unlike eye tracking systems which attempt to compensate for eye movements, eye stabilization systems can be used to effectively eliminate eye movements, and are generally more reliable and less complicated than eye tracking systems. In addition to eliminating eye movement, some eye stabilization systems can be used to establish a desirable alignment between the eye and the laser source. Moreover, the eye stabilization element can be attached to the laser system to establish and maintain an optimal (and known) optical path length between the eye and laser system.

One factor that is worthy of consideration when contemplating the use of an eye stabilization and alignment device is the comfort and safety of the patient. In this regard, eye stabilization devices typically apply a mechanical pressure to the eye for the purpose of restraining the eye. Generally, this pressure is applied to the surface of the eye (i.e. the sclera, limbus or cornea). For obvious reasons, large pressures applied to the eye are often uncomfortable to the patient and can result in post-operative pain and scarring. Moreover, the pressure can cause damage to the eye by increasing the intraocular pressure of the eye to dangerous levels.

For some eye stabilizing devices, a stabilizing element is first attached to the eye and thereafter the stabilizing element is aligned with and attached to a coupler or adapter on the laser source. For these types of devices, the pressures exerted on the eye during both stabilization and coupling to the laser source must be considered. In addition to the constraints described above, an eye stabilizing and alignment device must also be positioned such that it does not interfere with the laser procedure. Specifically, this implies that opaque portions of the device do not lie along the laser delivery beam path.

With regard to the process of aligning and attaching an eye to a laser system, as indicated above, this procedure must be carried out carefully to avoid the exertion of dangerous pressure levels on the eye. Heretofore, these alignment and "docking" procedures have generally been done manually. Specifically, this means that the movement of the eye relative to the laser system has needed to be observed visually by the surgeon and controlled by the hand of the surgeon. In these procedures, movements of the eye must be accommodated and corrected for and this often results in a relatively slow, labor intensive procedure, the satisfactory performance of which is highly dependent on the skill and patience of the surgeon.

In light of the above, it is an objective of the present invention to provide a device and method for aligning a patient's eye relative to a laser system to facilitate an engagement between the eye and laser system. Another object of the present invention is to provide an automated device for aligning a patient's eye relative to a laser system which does not rely exclusively on human eye hand coordination. Yet another object of the present invention is to provide a device and method for aligning and engaging a patient's eye with a laser system without damaging the eye. Still another object of the present invention is to provide a device and method for aligning a patient's eye relative to a laser system that is easy to use, relatively simple to manufacture, and comparatively cost effective.

SUMMARY OF THE INVENTION

The present invention is directed to a device for establishing a desired contact alignment between a patient's eye and a laser system. Once properly aligned, the eye can be safely engaged with the laser system to hold the eye stationary relative to the laser system. This fixed arrangement then allows a surgical beam to be accurately delivered from a source and focused to a selected ocular location.

As intended for the device of the present invention, a platform is provided for supporting the patient during a surgical procedure. Further, the platform is moveable relative to a laser system. Typically, the platform is configured for independent movement along each of three mutually orthogonal axes (e.g. x, y and z axes), and is moveable in response to a control signal from a system controller. In an alternate arrangement for the device of the present invention, the laser system can be mounted on the moveable platform, and the combination of platform and laser system can be reconfigured to control movement of the laser system relative to the patient's eye.

To determine a relative alignment between the eye and the laser system, the device includes a detector and, preferably, an illumination system also. In one embodiment, the illumination system is positioned and configured to directly illuminate the eye. Reflections from an anatomical feature of the eye are then imaged using a detector and this image, which is indicative of the spatial position of the eye, is transmitted to the system controller. Also for this embodiment, a marker can be mounted on the laser system to provide an indication of the laser system's position. Alternatively, a component of the laser system can be used for this purpose. In either case, the marker (or component) is then imaged using the detector. Then, along with the reflections from the eye, the marker (component) image is transmitted to the system controller. There, at the system controller, images of the respective spatial positions of the eye and the laser system are processed to determine a measured alignment of the eye relative to the laser system. This measured alignment is then compared to the desired alignment to determine an alignment difference. An error signal is then generated that is indicative of the alignment difference.

For the alignment device, the error signal from the system controller is used to incrementally move the platform in an appropriate direction. For example, the platform can be a motorized chair having a plurality of individually controllable stepper motors that are selectively energized in response to the error signal. After the first chair movement described above has been accomplished, a second image can be evaluated. This second image, which includes the marker and reflections from the eye, is detected and used to determine a more refined second alignment difference. This second alignment difference, in turn, is used by the system controller to generate a second error signal and cause a second chair movement. The process is then repeated, as many times as necessary, until the desired alignment between the eye and laser system is achieved (i.e. the alignment difference is zero).

In a particular embodiment of the present invention, the alignment device is used to align an eye stabilizing element (e.g. contact lens, suction ring, etc.) with the eye to facilitate an engagement between the eye and the eye stabilizing element. For this embodiment, the eye stabilizing element is first fixedly attached to the laser system. Once the eye stabilizing element is aligned with the eye as described above, the eye stabilizing element is advanced toward the eye to contact and engage an anterior surface of the eye. For example, the eye stabilizing element can contact and engage the cornea, limbus, sclera and combinations thereof.

In another embodiment, the eye stabilizing element is first installed on the eye for movement therewith. For example, a contact lens with an integral suction ring, or a suction ring alone, can be positioned on the eye and affixed thereto by the application of a suitable suction ring vacuum. For this embodiment, an adapter is mounted on the laser source for interaction with the eye stabilizing element. Specifically, the eye stabilizing element is formed with an engagement feature that can be coupled to a mating feature that is formed on the adapter.

It is to be appreciated that within the context of the present disclosure, several detector arrangements can be employed to create the image(s) necessary to align the eye with the laser system as described above. With the above caveat in mind, however, one arrangement of particular interest includes two detectors. For this arrangement, a first detector is positioned to create an image that indicates misalignments between the eye and laser system in a plane normal to a laser delivery beam path (i.e. misalignments in an x-y plane). On the other hand, the second detector is positioned to give positional information about the eye and laser system along the laser delivery beam path (i.e. in a z-direction). With this cooperation of structure, the alignment device can be used to initially align the eye and laser system (or, if applicable, the eye stabilizing element and adapter) in the x-y plane. Once aligned in the x-y plane, the eye can be moved in the z-direction toward the laser system. During this z-movement, the alignment device measures and maintains alignment in the x-y plane. Z-axis movement is then continued until the eye is engaged with the laser system (or, if applicable, the eye stabilizing element is engaged with the adapter).

In another aspect of the present invention, an embodiment of the alignment device can include a plurality of pressure sensors that are mounted on the laser system. More specifically, each sensor is positioned to measure a contact pressure between the eye and the laser system (or, if applicable, between the eye stabilizing element and the adapter). In one arrangement, three sensors are uniformly distributed around the laser delivery beam path and oriented to measure contact pressures that are directed parallel to the beam path. With this interactive cooperation of structure, the sensors can be used to perform one or more of the following functionalities: 1) to detect misalignments and augment the optical alignment device that is described above, 2) to ensure that dangerous pressure levels are not exerted on the patient's eye, and 3) to mechanically deform portions of the eye into a selected shape by placing a predetermined pressure gradient on the eye during engagement of the eye and laser system.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
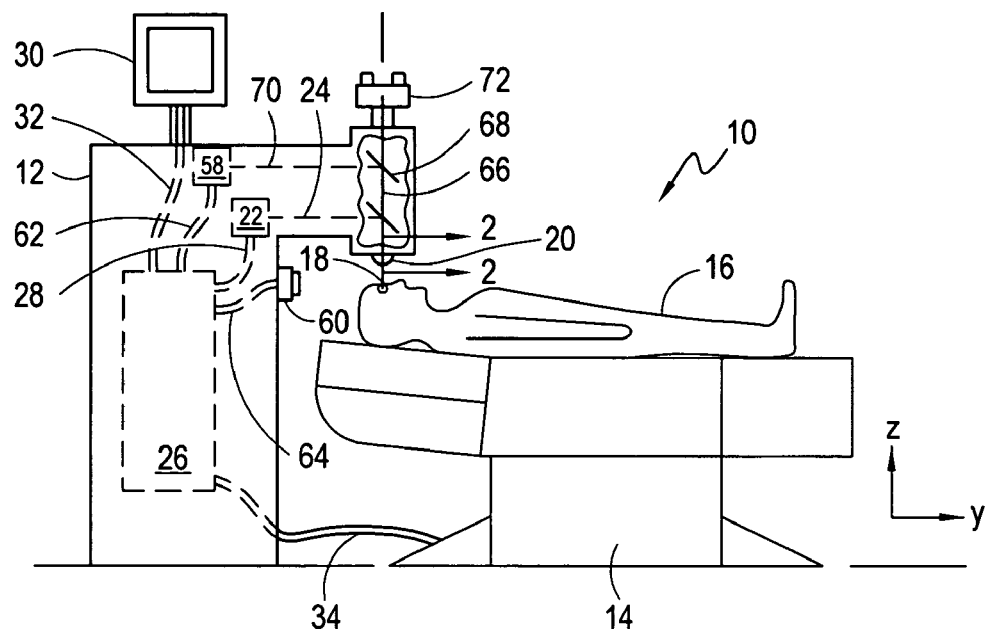
FIG. 1 is a front plan view of an apparatus for performing an ocular laser procedure on a patient having a device for aligning and engaging the patient's eye with a laser system, shown with portions broken away for clarity.

An apparatus for performing an ocular laser procedure is shown in FIG. 1 and is generally designated 10. As shown, the apparatus 10 includes a stationary surgical laser system 12 and a platform 14, which for the embodiment shown is a motorized chair. For the apparatus 10, the platform 14 is configured to support a patient 16, and is moveable to align the eye 18 of the patient 16 with an eye stabilizing element 20 which is rigidly attached to the laser system 12. On the other hand, the laser system 12 can be moved relative to the platform 14 to accomplish this same purpose. Once aligned, the platform 14 can be moved to engage the eye 18 with the eye stabilizing element 20.

For the apparatus 10, the laser system 12 also includes a laser source 22 for generating a laser beam and directing the beam along beam path 24, as shown. Laser source 22 is activated and controlled by a system controller 26 via cable 28. For the apparatus 10, the system controller 26 typically includes a software equipped computer processor. Also shown, the system controller 26 is connected to a graphical user interface 30 via cable 32 which is provided to receive instructions from, and present information to, a system operator (not shown).

FIG. 1 further shows that an electrical cable 34 connects the system controller 26 to the platform 14. Typically, the platform 14 is configured for independent movement along each of three mutually orthogonal axes (e.g. x, y and z axes) in response to a control signal from a system controller 26. These axes are shown in FIG. 1 (axes y and z) and FIG. 3 (axes x and y). For example, the platform 14 can be moved using three individually controllable stepper motors (not shown) that are selectively energized to move the platform 14 incrementally in response to the control signal.

Figure 2:
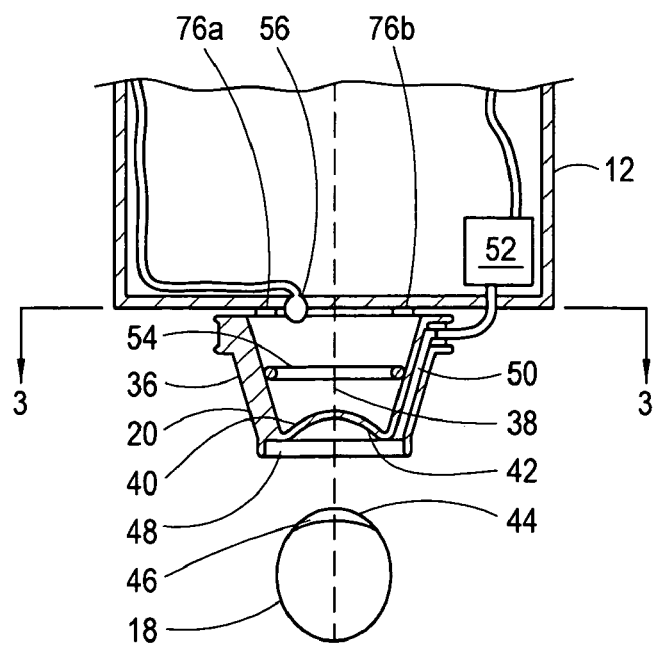
FIG. 2 is a cross sectional view of a portion of the apparatus of FIG. 1, as seen along the line 2-2 in FIG. 1.

FIG. 2 shows the eye stabilizing element 20 in greater detail. As shown there, the eye stabilizing element 20 is mounted on the laser system 12 and includes a hollow, base member 36 which is substantially shaped as a truncated cone and defines a longitudinal axis 38. The eye stabilizing element 20 also includes a curved lens 40 that is substantially centered on the axis 38 and is formed with a surface 42 for contacting the anterior surface 44 of the cornea 46 of the eye 18. For this purpose, the contact surface 42 of lens 40 will typically have a radius of curvature that is approximately 8.8 mm and be made of a clear, transparent material such as Poly(methyl) methacrylate. When a lens 40 is used, the eye 18 will be illuminated through the curved contact glass of the lens 40. The optical detectors 58 and 60 can then be used to detect the structure of the contact glass of the lens 40, as well as anatomical structures of the patient's eye (e.g. pupil, iris or retina). Alternatively, reflections of the illumination from the contact glass of the lens 40, and the anterior surface 44 of the eye 18 can be used for detection purposes.

As further shown in FIG. 2, the eye stabilizing element 20 includes a recessed vacuum channel 48 that is formed at the periphery of the lens 40. Additionally, a passageway 50 is formed in the base member 36 to establish fluid communication between the vacuum channel 48 and a vacuum pump 52. With this cooperation of structure, the eye stabilizing element 20 can be engaged with the eye 18. Specifically, as described further herein, the eye 18 is first aligned in the x-y plane (see FIG. 3) with the eye stabilizing element 20. Next, the eye 18 is moved toward the eye stabilizing element 20 until the anterior surface 44 of the cornea 46 contacts the surface 42 of the lens 40. At this point, the vacuum pump 52 is activated to establish a vacuum in the channel 48 to hold the eye 18 against the eye stabilizing element 20.

To align the eye 18 with the eye stabilizing element 20, the apparatus 10 includes a ring shaped marker 54 that is mounted on the eye stabilizing element 20 as shown in FIG. 2. As further shown, an illumination system 56 is positioned and configured to directly illuminate the eye 18. As shown in FIG. 1, the apparatus 10 also includes a pair of optical detectors 58, 60 (e.g. cameras) that are connected to the system controller 26 via respective cables 62, 64. Thus, with the illumination system 56 activated, reflections from the eye 18 and marker 54 traveling along beam path 66 are reflected by a dichroic (or partially silvered) mirror 68 and passed along beam path 70 to the detector 58. In addition, the dichroic (or partially silvered) mirror 68 allows a portion of the reflected light to be observed by the surgeon at a surgeon's microscope 72.

Figure 3:
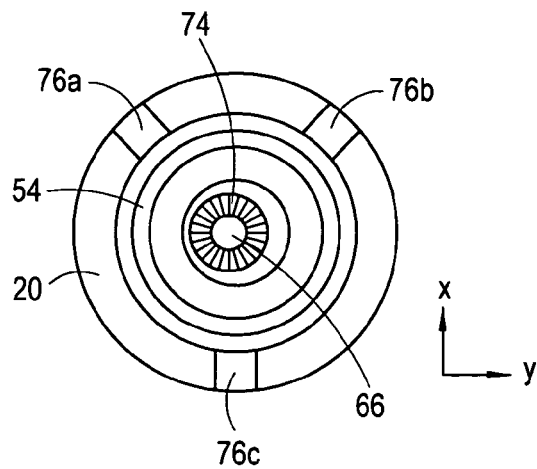
FIG. 3 is a view as seen along the line 2-2 in FIG. 1 showing a plurality of pressure sensors for measuring contact pressures during alignment and engagement of the eye with an eye stabilizing element.

FIG. 3 illustrates the relative position of the eye 18 and marker 54 as viewed by the detector 58. With this image, the system controller 26 can use an image processing algorithm to establish a measured alignment of the eye 18 relative to the eye stabilization element 20. For this purpose, the system controller 26 can determine the relative location of a specific anatomical feature of the eye 18, such as the iris 74, shown in FIG. 3. Alternatively, the pupil, the iris, or some non-anatomical feature, such as a mark (not shown) made on the eye 18, can be used to determine the relative alignment between the eye 18 and the marker 54, or some component of the laser system 12.

With cross reference to FIGS. 1 and 3, it is to be appreciated that a measured alignment of the eye 18 relative to the eye stabilizing element 20 in an x-y plane is established by the system controller 26 using an image obtained by the detector 58. Then, the system controller 26 compares the measured alignment to the desired alignment to determine an alignment difference and generates an error signal that is indicative of the alignment difference.

The error signal is then sent from the system controller 26 to the platform 14 where it is used to incrementally move the platform 14 in an appropriate direction. Typically, this involves the selective activation of a plurality of individually controllable stepper motors (not shown). After the first platform 14 movement described above, a second image which includes the marker 54 and reflections from the eye 18 is obtained by the detector 58 and used by the system controller 26 to determine a second alignment difference. This second alignment difference, in turn, is used by the system controller 26 to generate a second error signal and cause a second movement of platform 14. The process is then repeated, as many times as necessary, until the desired alignment in the x-y plane between the eye 18 and laser system 12 is achieved (i.e. the x-y alignment difference is zero). Moreover, the apparatus 10 can be used to maintain an alignment between the eye 18 and laser system 12 in spite of movements (i.e. involuntary movements) of the eye 18.

Once the eye 18 and eye stabilizing element 20 are aligned in the x-y plane as described above, the platform 14 is then moved in the z direction until contact is established between the anterior surface 44 of the cornea 46 and the surface 42 of the lens 40 (see FIG. 2). During this z movement, alignment in the x-y plane can be maintained using the detector 58 as described above. In addition, movements of the platform 14 in the z direction can be monitored by the optical detector 60 shown in FIG. 1.

Cross referencing FIGS. 2 and 3, it can be seen that three pressure sensors 76a-c are interposed between the eye stabilizing element 20 and the laser system 12. With this arrangement, each sensor 76a-c is positioned to measure a contact pressure between the eye 18 and the laser eye stabilizing element 20. For the apparatus 10, the pressure sensors 76a-c can be strain gauges or other sensors known in the pertinent art. Outputs from the pressure sensors 76a-c are provided to the system controller 26 via cables (not shown). As best seen in FIG. 3, the three sensors 76a-c are uniformly distributed around the laser delivery beam path 66 and oriented to measure contact pressures that are directed parallel to the beam path 66. With this structure, the sensors 76a-c can be used to ensure that dangerous pressure levels are not exerted on the eye 18. In addition, the sensors 76a-c can be used to detect misalignments and augment alignment using the detector 58.

More specifically, a misalignment between the eye 18 and eye stabilizing element 20 will result in pressure differences between adjacent pressure sensors 76a-c. The platform 14 can then be moved to reduce these pressure gradients and ensure correct alignment. In yet another implementation, the sensors 76a-c can be used to mechanically deform portions of the eye 18 into a selected shape by allowing a predetermined pressure gradient to be established during contact and engagement of the eye 18 and laser system 12.

Once proper contact has been established between the eye 18 and the eye stabilizing element 20, the vacuum pump 52 is activated to establish a vacuum in the channel 48 to hold the eye 18 against the eye stabilizing element 20. During activation of the vacuum pump 52, continuous monitoring by the pressure sensors 76a-c can be performed to ensure that dangerous pressure levels are not exerted on the eye 18.

Figure 4:
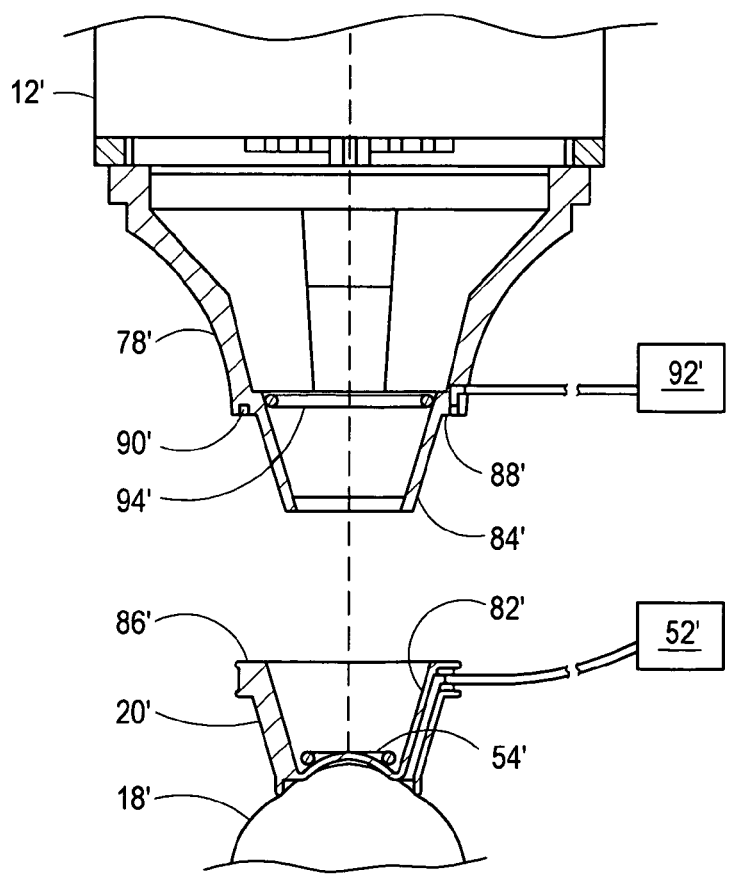
FIG. 4 is an exploded cross-sectional view of an eye stabilizing device in accordance with the present invention.

FIG. 4 illustrates another embodiment in accordance with the present invention in which the eye stabilizing element 20' is first installed on the eye 18' and held there by the application of suction from vacuum pump 52'. For this embodiment, an adapter 78' is mounted on the laser system 12' for engagement with the eye stabilizing element 20'. Specifically, as shown, the eye stabilizing element 20' and adapter 78' are formed with engagement features that allow the eye stabilizing element 20' to be coupled to and engage with the adapter 78'. These engagement features include an inner conical surface 82' formed on the eye stabilizing element 20' which contacts an outer conical surface 84' formed on the adapter 78'. During engagement, the eye stabilizing element 20' is advanced onto the adapter 78' until a rim 86' on the eye stabilizing element 20' contacts and abuts a shelf 88' that is formed on the adapter 78'. A suction can then be established in channel 90' by vacuum pump 92' to hold the eye stabilizing element 20' and adapter 78' together. A more detailed description of a suitable eye stabilizing element 20' and adapter 78' are provided in co-owned, co-pending U.S. patent application Ser. No. 10/790,625 filed Mar. 1, 2004 and entitled "System and Method for Positioning a Patient for Laser Surgery." The entire contents of U.S. patent application Ser. No. 10/790,625 are hereby incorporated by reference herein.

As further shown in FIG. 4, a marker 54' is mounted on the eye stabilizing element 20' and a marker 94 is mounted on the adapter 78'. With the structure, a detector, such as the detector 58 shown in FIG. 1, can be used to align the eye stabilizing element 20' with the adapter 78' as described above.

While the particular Device and Method for Aligning an Eye with a Surgical Laser and corresponding methods of use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A device for establishing a predetermined contact alignment between an eye of a patient and a laser system during ocular surgery which comprises:
   at least one detector for detecting a spatial position of the eye and a spatial position of the laser system;
   a controller means for determining an alignment difference between the spatial position of the eye and the spatial position of the laser system;
   a means for altering the alignment difference between the eye and the laser system to establish the predetermined contact alignment;
   a means for engaging the eye with the laser system to hold the eye stationary relative to the laser system to maintain the predetermined contact alignment;
   at least three pressure sensors mounted on the laser system for direct contact with the eye to individually measure a respective contact pressure on the eye during contact between the eye and the laser system; and
   a computer means for calculating a pressure differential between each sensor and each other sensor, wherein the altering means is activated by the computer means to establish predetermined pressure differentials.

2. A device as recited in claim 1 further comprising at least one pressure sensor mounted on the laser system for measuring a pressure on the eye during engagement between the eye and the laser system.

3. A device as recited in claim 2 further comprising a switch interconnecting the pressure sensor with the engaging means for stopping the engaging means whenever the pressure exceeds a predetermined level.

4. A device as recited in claim 1 wherein the altering means moves the patient.

5. A device as recited in claim 1 wherein the altering means moves the laser system.

6. A device as recited in claim 1 wherein the detector includes a camera.

7. A device as recited in claim 1 further comprising:
   a contact lens mounted on the laser system for engagement with the eye during the refractive surgery; and
   a marker positioned on the laser system, wherein the marker is indicative of the spatial position of the laser system.

8. A device as recited in claim 1 wherein the spatial position of the eye is determined by detecting an anatomical structure of the eye.

9. A device for aligning an eye of a patient with a surgical laser system and for facilitating a physical engagement therebetween, the device comprising:
   a detector for generating a control signal indicative on an alignment difference between a spatial position of the eye and a spatial position of the laser system;
   a motorized platform for supporting the eye and the laser system, the platform being reconfigurable in response to the control signal to effect a relative movement between the eye and the laser system to physically engage the eye of the patient with the laser system;
   at least three pressure sensors mounted on the laser system for direct contact with the eye to individually measure a respective contact pressure on the eye during contact between the eye and the laser system; and
   a computer means for calculating a pressure differential between each sensor and each other sensor, wherein the altering means is activated by the computer means to establish predetermined pressure differentials.

10. A device as recited in claim 9 wherein the detector comprises:
    a marker positioned on the laser system;
    an illumination system for creating a light pattern from the eye; and
    at least one camera for simultaneously imaging the marker and the light pattern for use in generating the control signal.

11. A device as recited in claim 10 further comprising a contact lens mounted on the laser system for physical engagement with the eye and wherein the marker is affixed to the contact lens.

12. A device as recited in claim 10 wherein the light pattern is created by reflections from an anatomical structure of the eye.

13. A device as recited in claim 10 wherein the light pattern is created by reflections from an exposed anterior surface of the eye.

14. A device as recited in claim 9 wherein the eye is attached to an eye stabilizing device and an adapter is mounted on the laser source and wherein the optical detection system is configured to receive light reflected from the eye stabilizing element to generate the control signal.

15. A device as recited in claim 9 wherein the platform supports and moves the patient.

16. A device recited in claim 9 wherein the detector comprises a camera for simultaneously detecting the spatial position of the eye and the spatial position of the laser system.

17. A method for aligning an eye of a patient with a surgical laser system and for facilitating a physical engagement therebetween, the method comprising the steps of:

configuring an optical detection system to generate a control signal indicative of an alignment difference between a spatial position of the eye and a spatial position of the laser system;

providing a motorized platform for supporting the eye and the laser system;

reconfiguring the motorized platform in an x-y plane in response to the control signal to effect a relative movement between the eye and the laser system to align the eye with the laser system;

reconfiguring the motorized platform in a z-direction to effect a relative movement between the eye and the laser system to physically engage the eye of the patient with the laser system;

measuring a respective contact pressure with three pressure sensors during contact between the eye and the laser system: and calculating a pressure differential between each sensor and each other sensor for use in the reconfiguring steps to establish predetermined pressure differentials.

18. A method as recited in claim 17 wherein the optical detection system comprises:

a marker positioned on the laser system;

an illumination system for creating a pattern from the eye; and at least one camera for simultaneously imaging the marker and the light pattern for use in generating the control signal.

\* \* \* \* \*